United States Patent
Yu et al.

(10) Patent No.: US 7,022,839 B2
(45) Date of Patent: Apr. 4, 2006

(54) HETERODIMERIC CONJUGATES OF NEOMYCIN-CHLORAMPHENICOL HAVING AN ENHANCED SPECIFICITY AGAINST RNA TARGETS AND ITS PREPARATION

(75) Inventors: Jaehoon Yu, Seoul (KR); Jongkook Lee, Seoul (KR); Miyun Kwon, Seoul (KR); Kye-Jung Shin, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 81 days.

(21) Appl. No.: 10/496,275

(22) PCT Filed: Dec. 5, 2001

(86) PCT No.: PCT/KR01/02101

§ 371 (c)(1),
(2), (4) Date: May 21, 2004

(87) PCT Pub. No.: WO03/044034

PCT Pub. Date: May 30, 2003

(65) Prior Publication Data

US 2005/0009765 A1    Jan. 13, 2005

(30) Foreign Application Priority Data

Nov. 23, 2001 (KR) ............... 2001-73358

(51) Int. Cl.
*C07H 1/00* (2006.01)
(52) U.S. Cl. .................... 536/123.1; 536/124

(58) Field of Classification Search .......... 514/39; 435/6; 536/123.1, 124
See application file for complete search history.

(56) References Cited

U.S. PATENT DOCUMENTS

| | | | |
|---|---|---|---|
| 884,713 A * | 4/1908 | Cherny | 249/162 |
| 5,143,545 A | 9/1992 | Stiffey et al. | |
| 5,411,941 A | 5/1995 | Grinna et al. | |
| 6,071,515 A | 6/2000 | Mezes et al. | |
| 6,235,469 B1 | 5/2001 | Kang et al. | |
| 6,316,194 B1 * | 11/2001 | Karn et al. | 435/6 |

OTHER PUBLICATIONS

Xavier et al. "RNA as a drug target: methods for biophysical characterization and screening," TIBTECH Aug. 2000 (vol. 18), pp. 349-356.*
Wells et al. "Pharacotherapy Handbook," 2nd addition, 1998, pp. 375-381.*
Bertram G. Katzung, Basic and Clinical Pharmacology, 7th edition, 1998, pp. 743-758.*

* cited by examiner

*Primary Examiner*—James O. Wilson
*Assistant Examiner*—Jason H. Johnsen
(74) *Attorney, Agent, or Firm*—Lucas & Mercanti, LLP

(57) ABSTRACT

The present invention relates to heterodimeric conjugates of neomycin-chloramphenicol, of formula 1, their preparation and their use. Because of their heterodmieric structure, they can recognize both stem and loop of RNA motif and show binding ability to a certain RNA such that they have an enhanced pharmaceutical efficacy and reduced side effect which can be caused by non-specific drugs. For these reasons, they can be effectively used as an antiviral agent, an antibacterial agent or an anticancer drugs.

6 Claims, No Drawings

HETERODIMERIC CONJUGATES OF NEOMYCIN-CHLORAMPHENICOL HAVING AN ENHANCED SPECIFICITY AGAINST RNA TARGETS AND ITS PREPARATION

This patent application claims the benefit of priority from Korean Patent Application No. 10-2001-0073358 filed on Nov. 23, 2001 through PCT application Ser. No. PCT/KR01/02101 filed on Dec. 5, 2001, the contents of each of which are incorporated herein by reference.

1. Technical Field

The present invention relates to heterodimeric conjugates of neomycin-chloramphenicol of formula 1, their preparation and their use as an antiviral agent, an antibacterial agent or an anticancer drug.

2. Background of the Invention

Currently most of the drugs use protein, the final product of genes, as target molecules, which take up 70–80% of the total drugs. However, as RNAs, which are products of genomes, were found to be pharmaceutical target molecules, intensive and extensive attention has been paid to anti-sense drugs capable of interacting with RNAS.

At first, it was thought that anti-sense type drugs, whose target molecules are mostly RNA molecules, could exert pharmaceutical effects by forming Watson-Crick base-pairs with target RNA molecules, thanks to their complementary base sequences. That is, it was thought that oligomeric RNA molecules whose base sequences are complementary to those of target RNA molecules could be anti-sense type drugs. However, research into the morphology of RNA target molecules revealed that whereas RNA target molecules exist in various dynamic forms, since the RNA target molecules are the anti-sense type drugs are not effective folded by self-base pairing to the most stable form.

In contrast to DNAs, RNAs have characteristic two- and three-dimensional structures resulting from self-base pairings. In an RNA molecule, bases are paired with other intramolecular bases to create a stem, while a stretch of non-paired bases forms an internal loop. The characteristic three-dimensional stem-loop structure is base sequence-specific, forming a stable pocket to which small molecules can bind well.

The pocket-like RNA structure to which active research has been recently directed can be easily found in ribosomes, which are in vivo protein factories. Ribosomal RNAs, which amount to half of the total weight of ribosomes, have two- or three-dimensional structures which are base sequence specific. Such base sequence-specific structures can play an important role in utilizing the ribosomal RNAs as target molecules. According to recent reports, it has been disclosed that 20 residues in the decoding region A site of 16S rRNA are highly conserved and are targeted by aminoglycoside, an RNA-binding compound. Aminoglycoside very specifically binds to rRNA. When aminoglycoside binds to an RNA molecule with a stem region, the stem structure is slightly widened to form an extended loop.

Besides a specific RNA of 16S rRNA, rRNAs include a variety of characteristic structures with specific base sequences. Therefore, because the rRNAs are verified as very good target molecules, the creation of compounds capable of specifically binding to them can lead to the development of promising materials or candidates that can inhibit the production of proteins of interest. Additionally, not only rRNAs, but also specific base sequences and corresponding characteristic RNA structures are discovered in a very wide spectrum of organisms, from viruses to higher organisms. For instance, in HIV viruses, some of their messenger RNAs for translating indispensable proteins have specific base sequences and corresponding steric structures (two- or three-dimensional structures). Rev binding proteins or TAR binding proteins are known to bind to such specific RNA motifs, functioning to activate the translation of the proteins necessary for the proliferation of the viruses. Located mainly in 5'-untranslated region (hereinafter referred to as "5'-UTR") or 3'-untranslated region (hereinafter referred to as "3'-UTR") of the translated proteins, such characteristic motifs are not directly involved in the translation of proteins. On the whole, they function to aid effective translation of proteins of interest, as in HIV viruses. The specific RNA motifs in 5'-UTR provide special conditions for protein translation and thus can be used as a way to control the translation of proteins.

A specific RNA motif, called internal ribosome entry site (IRES), which allows the mRNA to enter the ribosome and initiate translation without being scanned from the 5' end, was found in the 5'-UTR of piconavirus and hepatitis C virus (HCV). Recent reports have disclosed that the specific RNA motifs IRESs are located in the mRNAs present in the cytoplasm of many vertebrates as well as lower organism such as viruses. For example, characteristic IRES elements are found in the 5'-UTR of the mRNAs for human immunoglobulin heavy chain binding protein (BiP), heat shock protein 70 (HSP70), human fibroblast growth factor 2 (FGF2), and vascular endothelial growth factor (VEGF).

According to biological experiments, cells whose mRNAs for the proteins of interest are modified at their IRESs exhibit various biological changes which are not observed in normal cells. Particularly, the intracellular level of the IRES proteins found in the cytoplasm of higher animals is critical in determining their activity, indicating that the biosynthesis of the proteins is controlled in the post-transcriptional stage. Therefore, there is a high possibility that the IRESs of the cytoplasmic proteins be important target RNAs.

Aminoglycoside compounds capable of targeting RNAs are found in nature. Structurally characterized by plural hexose ring compounds, the naturally occurring aminoglycoside compounds have at least one functional amino group in each hexose ring. Neomycin, known to most efficiently bind to RNAs, has six amino acid moieties as well as many hydroxyl groups. There are various forms of aminoglycosides which differ in the positions and numbers of amino acids or hydroxyl groups from one to another.

The binding of aminoglycosides to their RNA targets is known to result from the electrostatic interaction between the amino groups of aminoglycoside and the phosphate of RNA which are positively and negatively charged, respectively, at physiological pH. Additionally, the hydroxyl groups or amide functional groups form hydrogen bonds with various functional groups of RNA, which also make a contribution to the binding of the aminoglycosides to their target RNAs.

Among various aminoglycosies, neomycin shows a relatively strong binding force to most RNA motifs, but is found to lack binding specificity. In fact, in order to better exert the pharmaceutical effects of neomycin, its binding force must be 100–1,000 fold improved from micromole levels to nanomole levels.

Generally, extensive and various attempts have been made to make compounds of low specificity highly specific. Aminoglycosides with no specific binding properties have been made to bind to specific RNAs in various ways. For example, first, there were suggested homodimers of aminoglycosides, with the aim of improving the binding to specific RNAs. Since an associated form of two identical sites with a certain binding force is generally known to show a more potent binding force, homodimers of aminoglucodies are expected to be more specific for some RNAs.

However, a significant change is observed in the binding force of a homodimer of aminoglycoside only when the RNA has two or more binding sites for the aminoglycoside, with no observation of a significant change in specificity for the compound. Alternatively, heterodimers are developed, in which aminoglycoside is associated with different kinds of compounds with new functional groups. Tor and his colleagues of Scripps Research Institute reported that a heterodimer in which acridine, a small compound, is associated with aminoglycoside, is about 100-fold more specific for the RRE RNA motif, compared to aminoglycoside alone. It was also found that the improvement in the specificity is attributed to the ability of the acridine moiety linked to the aminoglycoside moiety to recognize the bases located in the cleft of the RNA stem region. These research results demonstrate that the preparation of a compound connecting two molecules which can recognize two different sites in a RNA molecule, respectively, that is, the preparation of heterodimers, can bring about an improvement in both specificity and selectivity between aminoglycoside and RNA. In the present invention, the hetero-dimer strategy is adopted and expanded to develop RNA-specific drugs.

Leading to the present invention, the intensive and thorough research into RNA-specific drugs, conducted by the present inventors with the aim of solving problems encountered in prior arts, resulted in the finding that neomycin-chloramphenicol heterodimers, in which neomycin is linked through a spacer to chloramphenicol, can more strongly bind to specific RNAs and recognize both the stems and loops of the RNA molecules, with base sequence specificity.

DISCLOSURE OF THE INVENTION

The present invention relates to neomycin-chloramphenicol heterodimer represented by following formula 1.

structure which connects the main structure of neomycine and chloramphenicol with a spacer having carbon chains of a suitable length.

Particulary, among chloramphenicol and aminoglycoside, known to show a strong binding force to RNA loops, neomycin showing the strongest binding force to RNAs was bound using a site the least affected by the pharmaceutical effect of the two compounds as a spacer. The spacer comprises dimercapto compounds, preferably the carbon number of the spacer is 3, 6 or 9.

The neomycin-chloramphenicol heterodimer can recognize both stems and loops which are usually discovered at the structure of RNA. In the accordance with the below embodiments, as a result of measuring the binding force of the neomycin-chloramphenicol heterodimer with 16S RNA, an RNA with the known two- or three-dimensional structures, RRE RNA known as a target RNA of HIV, and TS RNA playing an important role in the metabolism of higher organisms, they showed a more potent binding force than the known neomycin. Particularly, the neomycin-chloramphenicol heterodimer of the following example 2 wherein n is 6 showed a potent binding force below 10 nM by specifically binding with 16S rRNA, and showed an increase of 200 times in specificity compared with neomycin (2 microM). The increase of specificity of the neomycin-chloramphenicol heterodimer was not observed in other RNA motifs, which is determined by specific base sequences comprising stems and loops containing 16S rRNA, not by the general increase of the binding force recognizing the stems and loops at the same time.

The present invention comprises a method for preparing neomycin-chloramphenicol heterodimer represented by the following reaction scheme 1, which particularly comprises steps of;

Reacting (1R,2R)-2-(9-bromoacetylamido)-1-(4-nitrophenyl)-1,3-t-butyldimthylsilyloxypropane (formula 2) with

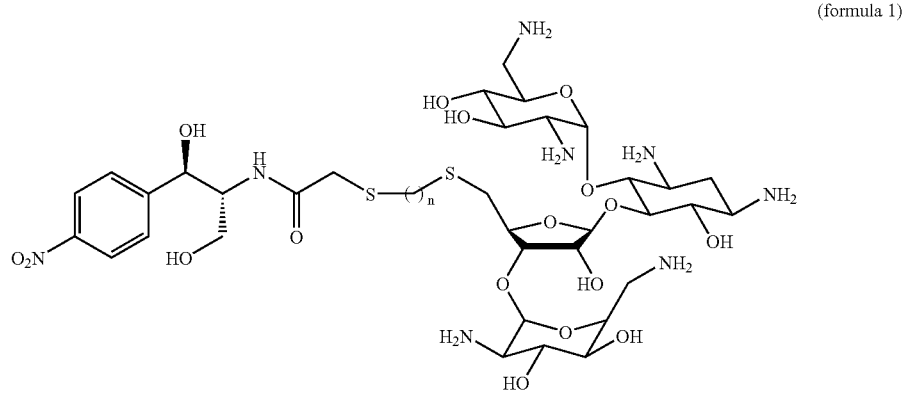

(formula 1)

wherein, n is an integer of 2–10, preferably 3, 6 or 9.

As above represented by formula 1, the neomycin-chloramphenicol of heterodimer the present invention has a the compound of formula 3 in the presence of base to obtain the compound of formula 8 (step 1); and Reacting the obtained compound of formula 8 with a deprotective agent to prepare the neomycin-chloramphenicol heterodimer (step 2).

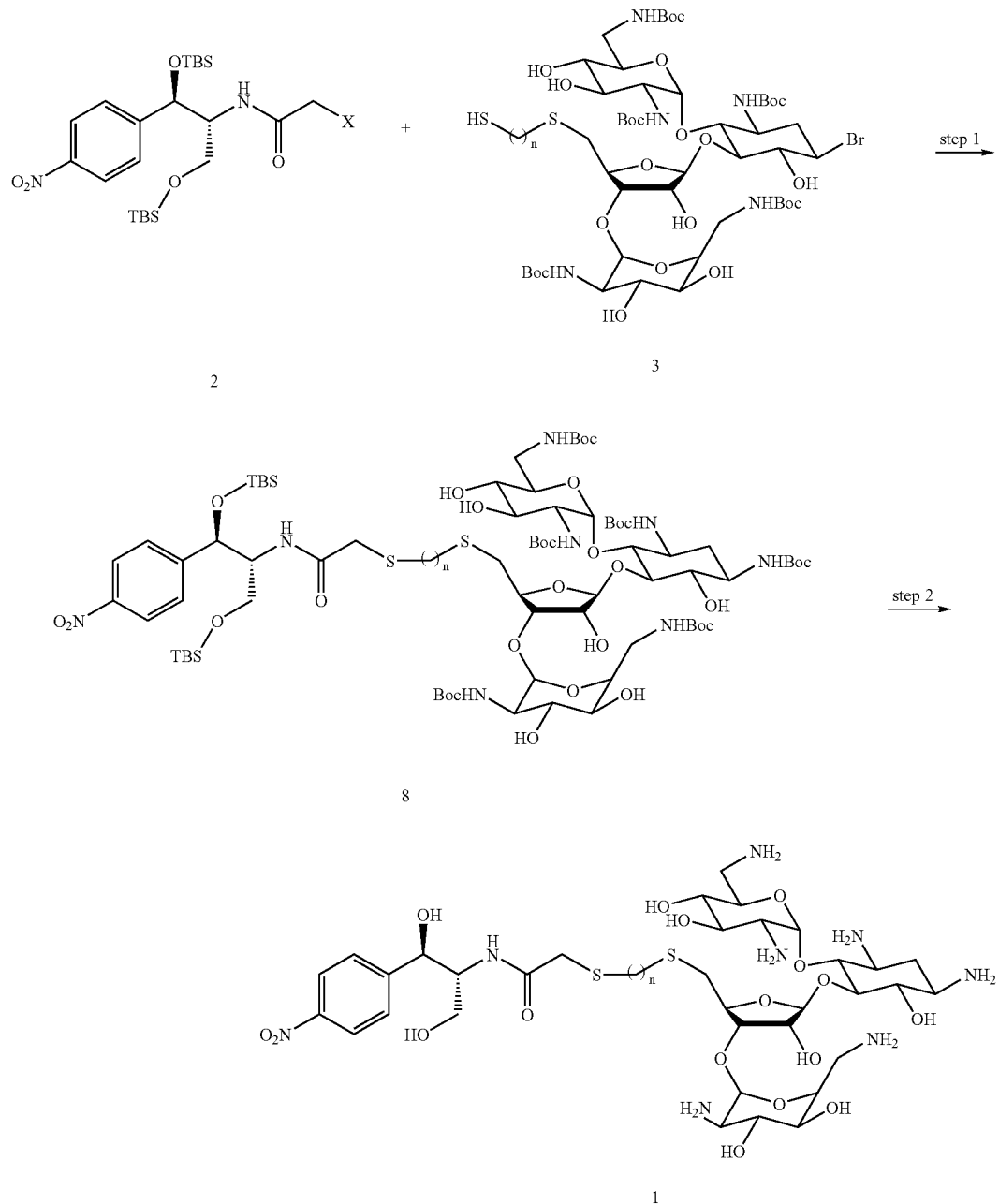

(reaction scheme 1)

wherein, X is a halogen, n is an integer of 2–10, preferably 3, 6 or 9.

In step 1, the compound of formula 2 is reacted with the compound of formula 3 in the presence of base at room temperature for 5–10 hours to obtain the compound of formula 8. The base is $K_2CO_3$, $Na_2CO_3$ or $Cs_2CO_3$, preferably $Cs_2CO_3$. At this time, a used solvent is dimethylforamide, dimethyl sulfoxide or acetonitrile, preferably dimethylforamide.

In step 2, the deprotective agent, to deprotect silyl group of formula 8, is tetrabutylamoniumfloride, hydrofluoric acid, hydrofluoric acid pyridine salt, hydrochloric acid, sulfuric acid or nitric acid, preferably tetrabutylamoniumfloride, or to deprotect t-butylcarbonyl, is hydrochloric acid, sulfuric acid, acetic acid or trifluoroacetic acid, preferably trifluoroacetic acid.

Also, as above presented by following reaction scheme 1, the compounds of formula 2 and formula 3 can be prepared using various methods.

For example, the compound of formula 2, as the following reaction scheme 2, comprises steps of;

reacting (1R,2R)-(−)-2-amino-1-(4-nitrophenyl)-1,3-propandiol with 9-fluorenylmethyl carbonate to obtain the compound of formula 4 protected with 9-fluorenylmethyloxycarbonyl group (step 1);

reacting the compound of formula 4 with t-butylmethyl-silyltriplate to obtain the compound of formula 5 wherein alkoxy group is with protected t-butyldimethylsilyl group (step 2);

reacting the compound of formula 5 with piperidine to obtain the compound of formula 6 deprotected only with amine group (step 3); and reacting the compound of formula 6 with acylating agent in the presence of base to obtain the compound of formula 2 (step 4).

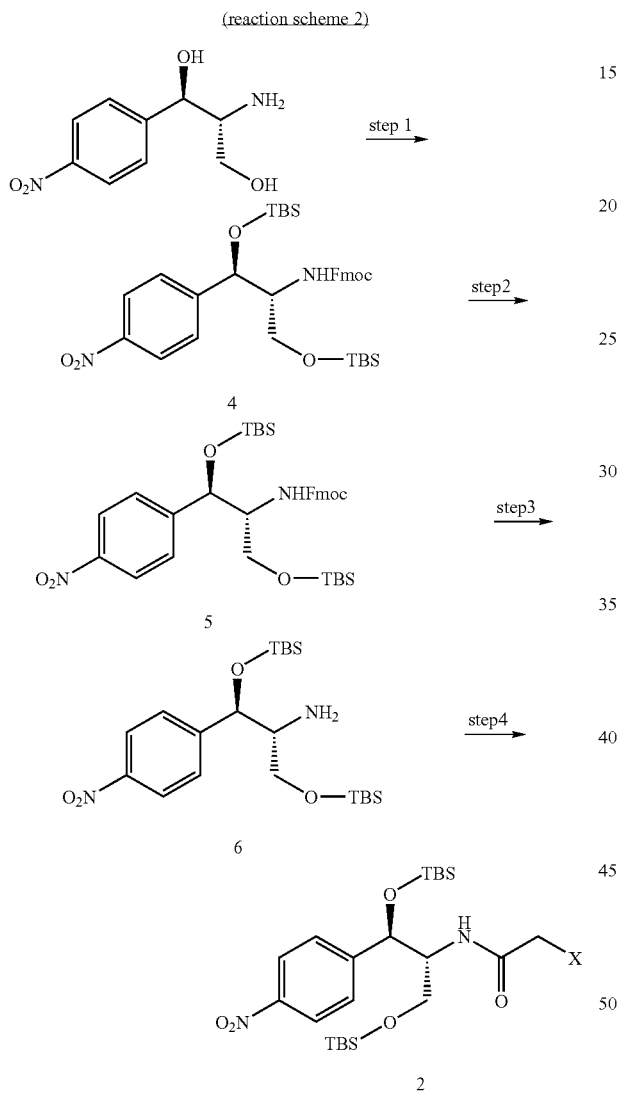

wherein,
TBS is a t-butyldimethylsilyl
X is halogen.

In step 1, wherein amine group is protected with 9-fluorenylmethyloxycarbonyl group, a protective agent is 9-fluorenylmethyl chloroformate or 9-fluorenylmethyl pentafluorophenyl carbonate. It is also preferred for yield and reactivity if the base of a mixture solution comrising 9-fluorenylmetyl succinimido carbonate, ether and water is NaHCo$_3$.

In step 2, wherein alkoxy group is protected with t-butylmethylsilyl group t-butyldimethylsilyltriplate is reacted with the compound of formula 4 in the presence of carbon dichloride at 0° C. to protect both t-butyldimethylsilyl group and first and second alkoxy group.

In step 3, wherein an alternative deprotecting reaction of the amine group protected with 9-fluorenylmethyloxycarbonyl group is performed, the reaction was performed at room temperature using carbon dichloride as solvent, and 20% of piperidine.

In step 4, wherein the compound of formula 6 is reacted with amine group in the presence of carbon dichloride at 0° C., a acylation reagent is bromoacetylbromide, bromoacetylchloride, chloroacetylbromide or chloroacetylchloride, preferably bromoacetylbromide. The base is aromatic amine such as pyridine and lutidine or aliphatic amine such as diisopropylethylamine, preferably pyridine.

The compound of above formula 3, represented by the following reaction scheme 3, is obtained by reacting the compound of formula 7 with dimercapto compound in the presence of base.

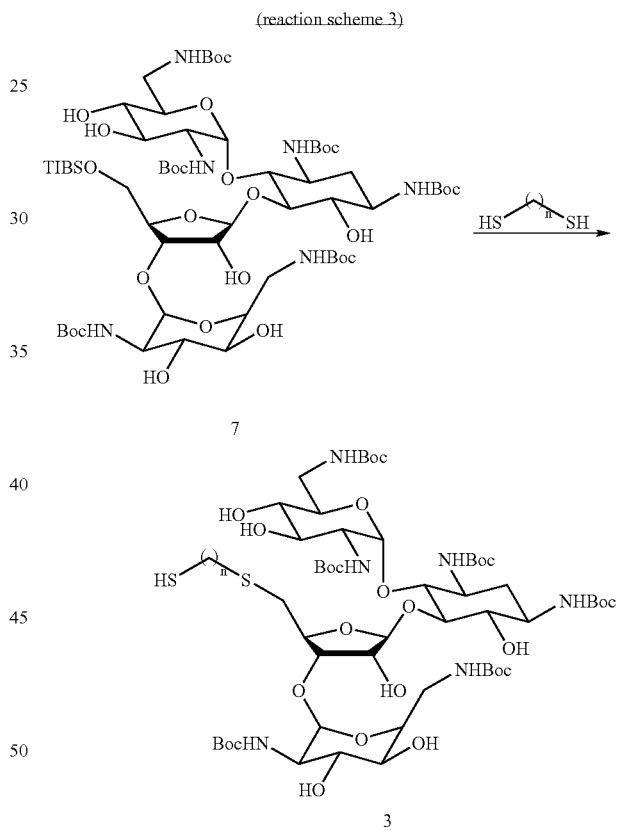

wherein,
n is an integer of 2–10, preferably 3, 6, or 9.

The compound which protect amine represented by formula 7 with t-butyloxycarbonyl group and substituted the first alcohol group with triisopropylsulfonyl group is prepared by a conventional method of preparing neomycine.

Particularly, dimercapto compound is reacted with the compound of formula 7 in the presence of base to obtain the compound of formula 3. Preferably, the dimercapto compound is 1,3-propanditiol, 1,6-hexanditiol or 1,9-nonanditiol, the base is K$_2$CO$_3$, Na$_2$CO$_3$ or Cs$_2$CO$_3$, and the solvent is DMF, DMSO or acetonitrile.

Also, the present invention comprises an antiviral agent, an antibacterial agent and an anticancer drug having heterodimeic conjugates of neomycin-chloramphenicol as an active ingredient.

That is, the heterodimeic conjugates of neomycin-chloramphenicol can be formulated into various dosage forms for oral or parenteral administration. For formulation, pharmaceutically acceptable diluents, expedients and/or carriers may be used, including fillers, thickeners, binders, wetting agents, disintegrants, surfactants, etc. Solid dosage forms for oral administration are exemplified by tablets, pills, powders, granules, and capsules. These solid forms are prepared by admixing neomycine-chloramphenicol heterodimer of formula 1 with at least one expedient, such as starch, calcium carbonate, sucrose, lactose, gelatine, etc. In addition to expedients, lubricants such as magnesium styrate may be added.

Liquid dosage forms for oral administration exemplified by suspensions, internal solutions, emulsions, syrups, etc., may comprise simple diluents, such as water and liquid paraffin, as well as wetting agents, sweeteners, aromatics, and/or perspectives.

Dosage forms for parenteral administration include sterile aqueous solutions, non-aqueous solvents, suspensions, emulsions, freeze-dried agents, suppositories, etc. For formulation of non-aqueous solvents and suspensions, vegetable oils, such as propylene glycol and polyethylene glycol, olive oil or injectable esters such as ethyl oleate, may be used. As basee for syppositories, witepsol, macrogol, Tween 61, cocoa oil, laurinic acid, and glycerogelatine are useful.

The amount of the active ingredient actually administered ought to be determined in light of various relevant factors including the absorptance of active components in vivo, the water active values, the rate of excretion, the age, sex and body of the individual subject, and the severity of the subject's symptoms. In genernal, the compound of neomycin-chloramphenicol heterodimer may be administered in a total dose of 0.1–50 mg per 1 kg a day to adults in 1 or various administrations, preferably, 0.1–10 mg per 1 kg.

A better understanding of the present invention may be obtained in light of the following examples which are set forth to illustrate, but not construed to limit the present invention.

EXAMPLE

Preparation Example 1

Preparation of (1R,2R)-2-bromoacetylamido-1-(4-nitrophenyl)-1,3-t-butyldimethylsilyloxypropane The preparation is accomplished as the following reaction scheme.

(Step 1) Preparation of (1R,2R)-2-(9-fluorenylmethylcarbamoyl)-1-(4-nitropheyl)-1,3-propandiol 3.00 g of (1R,2R)-(−)-2-amino-1-(4-nitrophenyl)-1,3-propandiol, and 28 ml of $NaHCO_3$ solution were mixed with 140 ml of ether. Subsequently, 4.77 g of 9-fluorenylmethyl succinimido carbonate was added to the reaction solution, and stirred for 24 hours. The reacted mixture was poured into 1 N of hydrochloric acid solution. At this time, the two-obtained white precipitate was eliminated by filter paper. The eliminated residue was separated and organic layer was obtained. The organic layer was washed with a mixture of a diluted solution of hydrochloric acid and saturated sodium chloride solution. The organic layer was dried with anhydrous $MgSO_4$ and concentrated in vacuo to obtain white solid. The white solid was recrystallized using the EtOAc/Hexane mixture solvent system to obtain 5.83 g of a white crystal, (1R,2R)-2-(9-fluorenylmethylcarbamoil)-1-(4-nitrophenyl)-1,3-propandiol. The yield is 95%.

$^1$H NMR ($CD_3OD$, 300 MHz) δ 8.13 (d, J=8.7 Hz, 2H), 7.79 (d, J=7.4 Hz, 2H), 7.62–7.55 (m, 4H), 7.39 (t, J=7.3 Hz, 2H), 7.32–7.26 (m, 2H), 5.08 (s, 1H), 4.30–4.08 (m, 3H), 3.91–3.86 (m, 1H), 3.80–3.74 (m, 1H), 3.59–3.49 (m, 1H).

(Step 2) Preparation of (1R,2R)-2-(9-fluorenylmethylcarbamoile)-1-(4-nitrophenyl)-1,3-t-butyldimethyloxypropane 67 ml of carbon dichloride was added to 2.90 g of (1R,2R)-2-(9-fluorenylmethylcarbamoile)-1-(4-nitophenyl)-1,3-propandiol and stirred. 3.1 ml of 2,6-lutidine and 4.6 ml of t-butyldimethylsilyltriflate was added to the mixture at 0° C., and stirred at the same temperature for 4 hours. The reacted mixture was diluted with carbon dichloride, and then was washed with hydrochloric acid dilutent and saturated brine. The mixture was dried with anhydrous $Na_2SO_4$ and concentrated in vacuo. The residue was purified with silicagel column chromatography (EtOAc:hexane=1:10), to obtain a cyrup type (1R,2R)-2-(9-fluorenylmethylcarbamoyl)-1-(4-nitrophenyl)-1,3-t-butyldimethylsilyloxypropane (99 mg). The yield is 95%.

$^1$H NMR ($CDCl_3$, 300 MHz) δ 8.18 (d, J=8.6 Hz, 2H), 7.79 (d, J=7.5 Hz, 2H), 7.57–7.28 (m, 8H), 5.20 (d, J=2.0 Hz, 1H), 5.11 (d, J=9.0 Hz, 1H), 4.33 (d, J=7.1 Hz, 2H), 4.20 (d, J=6.9 Hz, 1H), 3.79–3.75 (m, 1H), 3.62 (d, J=7.1 Hz, 2H), 0.98–0.90 (m, 18H), 0.14–0.06 (m, 6H).

(Step 3) Preparation of (1R,2R)-2-amino-1-(4-nitrophenyl)-1,3-t-butyldimethylsilyloxypropane 3.70 g of (1R,2R)-2-(9-fluorenylmethylcarbamoyl)-1-(4-nitrophenyl)- 1,3-t-butyldimethylsilyloxypropane and 4.0 ml of piperidine was added to 16.0 ml of DMF (dimethylformamide) and stirred at room temperature for 1 hour. The reacted mixture was poured into water and an organic layer was extracted using 150 ml of ethylacetate for 3 times. The extracted organic layer was collected and washed with brine. And then, the layer was dried with anhydrous $Na_2SO_4$ and concentrated in vacuo. The residue was purified with silicagel column chromatography (EtOAc:hexane=1:10) to obtain a cyrup type (1R,2R)-2-amino-1-(4-nitrophenyl)-1,3-t-butyldimethylsilyloxypropane (2.47 g). The yield is 98%.

$^1$H NMR ($CDCl_3$, 300 MHz) δ 8.21 (d, J=8.6 Hz, 2H), 7.49 (d, J=8.7 Hz, 2H), 4.90 (d, J=4.4 Hz, 2H), 3.55 (dd, J=10.0, 6.3 Hz, 1H), 3.40 (dd, J=10.0, 5.1 Hz, 1H), 2.77–2.71 (m, 1H), 0.94 (s, 9H), 0.93 (s, 9H), 0.09 (s, 3H), 0.07 (s, 6H), −0.13 (s, 3H).

(Step 4) Preparation of (1R,2R)-2-bromoacetylamido-1-(4-nitrophenyl)-1,3-t-butyldimethyloxypropane 1.67 g of (1R,2R)-2-amino-1-(4-nitrophenyl)-1,3-t-butyldimethylsilyloxypropane was dissolved in 12.6 ml of carbon dichloride, and 0.77 ml of pyridine and 0.43 ml of bromoacetyl bromide was added to the solution at 0° C. After the solution was stirred at the same temperature for 1 hour, the reacted mixture was diluted with ethylacetate and washed with saturated brine. The washed solution was dried with anhydrous $Na_2SO_4$ and concentrated in vacuo. The residue was purified with silicagel column chromatography (EtOAc:hexane=1:10) to obtain a cyrup type (1R,2R)-2-bromoacetylamido-1-(4-nitrophenyl)-1,3-t-butyldimethylsilyloxypropane (2.00 g). The yield is 94%.

$^1$H NMR ($CDCl_3$, 300 MHz) δ 8.18 (d, J=8.7 Hz, 2H), 7.47 (d, J=8.6 Hz, 2H), 7.07 (d, J=8.9 Hz, 1H), 5.21 (d, J=2.2 Hz, 1H), 3.98–3.90 (m, 1H), 3.85 (d, J=14.2 Hz, 1H), 3.75 (d, J=14.2 Hz, 1H), 3.63–3.52 (m, 2H), 0.95 (s, 9H), 0.93 (s, 9H), 0.12 (s, 3H), 0.10 (s, 3H), 0.08 (s, 3H), −0.15 (s, 3H).

Preparation Example 2

Preparation of Neomycine Wherein Amine is Protected with t-Butyloxycarbonyl and the First Alkoxy Substituted group is with Carbon Chain Containing a Mercapto Group The reaction was performed in the manner represented by the following reaction scheme 3.

(when, n=3)

880 mg of the compound of formula 7 was dissolved in 11.8 mg of DMF, and then 0.48 ml of 1,3-propane-di-thiol and 365 mg of $Cs_2CO_3$ were added to the mixture at room temperature. After the mixture was stirred at room temperature for 9 hours, the mixture was poured into water. The mixture was extracted using 100 ml of EtOAc for 3 times. The extracted organic layer was collected and washed with saturated brine. The washed organic layer was dried with anhydrous $Na_2SO_4$ and concentrated in vacuo. The residue was purified with silicagel column chromatography ($CH_2Cl_2$:MeOH=15:1) to obtain a white solid compound of formula 3 (n=3) (680 mg). The yield is 88%.

$^1$H NMR ($CD_3OD$, 300 MHz) δ 6.43 (br s, 1H), 5.38 (s, 1H), 5.14 (s, 1H), 4.93 (s, 1H), 4.25 (s, 1H), 4.11 (d, J=4.8 Hz, 1H), 3.90–3.82 (m, 2H), 3.76–3.68 (m, 2H), 3.58–3.19 (m, 15H), 3.11 (t, J=6.6 Hz, 1H), 2.75 (t, J=6.9 Hz, 2H), 2.63 (t, J=6.9 Hz, 2H), 2.03–1.75 (m, 3H), 1.47–1.29 (m, 55H).

(when n=6)

1.0 g of the compound of formula 7 was dissolved in 13.4 ml of DMF, and then 0.82 ml of 1,6-hexane-di-thiol and 414 mg of $Cs_2CO_3$ were added to the mixture at room temperature. After the mixture was stirred at room temperature for 9 hours, the reacted mixture was poured into water, and then was extracted using 100 ml of EtOAc for 3 times. The extracted organic layer was collected and washed with saturated brine. The washed organic layer was dried with anhydrous $Na_2SO_4$ and concentrated in vacuo. The residue was purified with silicagel column chromatography ($CH_2Cl_2$:MeOH=15:1) to obtain a white solid compound of formula 3 (n=6) (773 mg). The yield is 85%.

$^1$H NMR ($CDCl_3$, 300 MHz) δ 6.20 (br s, 1H), 5.14 (s, 1H), 5.05 (s, 1H), 4.96 (s, 1H), 4.13–3.15 (m, 25H), 2.72–2.60 (m, 2H), 2.50–2.40 (m, 4H), 1.66–1.30 (m, 64H).

(when n=9)

1.00 g of the compound of formula 7 was dissolved in 13.4 ml of DMF, and then 1.1 ml of 1,9-nonane-di-thiol and 414 mg of $Cs_2CO_3$ were added to the mixture at room temperature. After the mixture was stirred at room temperature for 9 hours, the reacted mixture was poured into water, and then was extracted using 100 ml of EtOAc for 3 times. The extracted organic layer was collected and washed with saturated brine. The washed organic layer was dried with anhydrous $Na_2SO_4$ and concentrated in vacuo. The residue was purified with silicagel column chromatography ($CH_2Cl_2$:MeOH=15:1) to obtain a white solid compound of formula 3 (n=9) (706 mg). The yield is 76%.

$^1$H NMR ($CDCl_3$, 300 MHz) δ 6.06–5.90 (m, 2H), 5.50–4.84 (m, 8H), 4.03–2.95 (m, 25H), 2.72–2.20 (m, 6H), 1.52–1.11 (m, 70H).

Example 1

Preparation of Neomycin-Chloramphenicol Heterodimer (n=3) I (Step 1): Preparation of Protected Neomycin-Chloramphenicol Heterodimer 450 mg of the compound of formula 3 (n=3) and 168 mg of $Cs_2CO_3$ was added to 3.4 ml of DMF. 300 mg of the compound of formula 2 dissolved in 1 ml of DMF was added to the obtained solution and then stirred at room temperature for 72 hours. The obtained mixture was poured into water and extracted using 70 ml of EtOAc for 3 times. Then, the extracted organic layer was collected and the organic layer was washed with saturated brine. The washed organic layer was dried with anhydrous $Na_2SO_4$ and concentrated in vacuo. The residue was purified with silicagel column chromatography (CH2Cl2:MeOH=15:1) to obtain a white solid protected neomycin-chloramphenicol (formula 8 (n=3), 192 mg). The yield is 31%.

$^1$H NMR ($CDCl_3$, 300 MHz) δ 8.18 (d, J=8.6 Hz, 2H), 7.47 (d, J=8.6 Hz, 2H), 7.33 (d, J=8.6 Hz, 1H), 6.15 (d, J=8.5 Hz, 1H), 5.98 (br s, 1H), 5.51 (br s, 2H), 5.25 (s, 1H), 5.14 (s, 1H), 5.08 (s, 1H), 4.96 (s, 1H), 4.15–3.10 (m, 18H), 2.85–2.30 (m, 8H), 2.01–1.79 (m, 3H), 1.45–1.41 (m, 55H), 0.97 (s, 9H), 0.93 (s, 9H), 0.12 (s, 3H), 0.11 (s, 3H), 0.09 (s, 3H), −0.12 (s, 3H).

(Step 2): Preparation of Heterodimeric Conjugates of Neomycin-Chloramphenicol 0.12 ml of tetrabutylamoniumfluoride (1.0 M of tetrahydrofuran solution) was added to solution of 74 mg of the compound of formula 8 (n=3) and 0.8 ml of tetrahydrofuran, and then was stirred at room temperature for 2 hours. The obtained mixture was dried and concentrated in vacuo. The residue was dissolved in EtOAc and washed with 0.5 N of hydric acid and saturated brine. The washed residue was dried with anhydrous $Na_2SO_4$ and concentrated in vacuo. The concentrated residue was purified with silicagel column chromatography ($CH_2Cl_2$:MeOH=15:1) to obtain a white solid compound (51 mg). 1 ml of trifluoroacetic acid was added to the obtained compound and then stirred at room temperature for 1 hour. The mixture was concentrated in vacuo. The residue was filtered using a silicagel column and then purified with semiprep-HPLC (RP-C18 column, $H_2O$ comprising 0.1% of TFA:MeCN comprising 0.1% of TFA=70:30) to obtain a salt of trifluoroacetic acid of neomycine-chloramphenicol heterodimer (n=3, 30 mg, solid of white). The yield is 36%.

$^1$H NMR (D$_2$O, 300 MHz) δ 8.06 (d, J=8.7 Hz, 2H), 7.47 (d, J=8.7 Hz, 2H), 5.87 (d, J=3.7 Hz, 1H), 5.21 (d, J=2.1 Hz, 1H), 5.13 (s, 1H), 5.02 (d, J=2.3 Hz, 1H), 4.24–4.04 (m, 6H), 3.95–2.80 (m, 22H), 2.68–2.44 (m, 2H), 2.37–2.23 (m, 3H), 2.14–1.90 (m, 2H), 1.82–1.43 (m, 3H), 1.13–1.03 (m, 1H);

$^{13}$C NME (D$_2$O, 75 MHz) δ 172.8, 163.4 (q, J=35.2 Hz), 150.1, 147.3, 127.4, 124.0, 116.8 (q, J=289.9 Hz), 110.8, 96.1, 95.4, 86.0, 80.6, 79.1, 76.2, 74.2, 73.0, 71.2, 71.1, 70.5, 69.8, 68.5, 68.0, 67.8, 61.8, 56.9, 54.1, 51.3, 50.2, 48.9, 40.9, 40.7, 35.2, 34.6, 30.8, 30.7, 23.8.

Example 2

Preparation of Neomycin-Chloramphenicol Heterodimer (n=6) II (Step 1): Preparation of Protected Neomycin-Chloramphenicol Heterodimer 326 mg of the compound of formula 3 (n=6) and 98 mg of Cs$_2$CO$_3$ were added to 3.0 ml of DMF and mixed. 170 mg of the compound of formula 2 dissolved in 1 ml of DMF was added to the obtained solution and then stirred at room temperature for 8 hours. The obtained mixture was poured into water and extracted using 70 ml of EtOAc for 3 times. Then the extracted organic layer was collected and the organic layer was washed with saturated brine. The washed organic layer was dried with anhydrous Na$_2$SO$_4$ and concentrated in vacuo. The residue was purified with silicagel column chromatography (CH$_2$Cl$_2$:MeOH=15:1) to obtain a white solid protected neomycin-chloramphenicol heterodimer (formula 8 (n=6), 383 mg). The yield is 87%.

$^1$H NMR (CDCl$_3$, 300 MHz) δ 8.16 (d, J=8.7 Hz, 2H), 7.46 (d, J=8.6 Hz, 2H), 7.39 (d, J=8.6 Hz, 1H), 6.15–5.90 (m, 2H), 5.25 (s, 1H), 5.13–5.11 (m, 2H), 4.95 (s, 1H), 4.15–3.00 (m, 25H), 2.79–2.18 (m, 8H), 1.79–1.33 (m, 64H), 0.96 (s, 9H), 0.93 (s, 9H), 0.12 (s, 3H), 0.11 (s, 3H), 0.08 (s, 3H), −0.13 (s, 3H).

(Step 2): Preparation of Heterodimeric Conjugates of Neomycin-Chloramphenicol 0.40 ml of tetrabutylamoniumfluoride (1.0 M of tetrahydrofuran solution) was added to a solution of 245 mg of the compound of formula 8 (n=6) and 2.6 ml of tetrahydrofuran, and then was stirred at room temperature for 2 hours. The obtained mixture was dried and concentrated in vacuo. The residue was dissolved in EtOAc and washed with 0.5 N of hydric acid and saturated brine. The washed residue was dried with anhydrous Na$_2$SO$_4$ and concentrated in vacuo. The concentrated residue was purified with silicagel column chromatography (CH$_2$Cl$_2$:MeOH=15:1) to obtain a white solid compound (184 mg). 3 ml of trifluoroacetic acid was added to the obtained compound and then stirred at room temperature for 1 hour. The mixture was concentrated in vacuo. The residue was filtered using a silicagel column and then purified with semiprep-HPLC (RP-C18 column, H$_2$O comprising 0.1% of TFA:MeCN comprising 0.1% of TFA=70:30) to obtain a salt of trifluoroacetic acid of neomycine-chloramphenicol heterodimer (n=6, 117 mg, solid of white). The yield is 49%.

$^1$H NMR (D$_2$O, 300 MHz) δ 8.17 (d, J=8.7 Hz, 2H), 7.58 (d, J=8.7 Hz, 2H), 6.05 (d, J=3.9 Hz, 1H), 5.35 (s, 1H), 5.24 (s, 1H), 5.14 (d, J=2.0 Hz, 1H), 4.39 (s, 2H), 4.30–4.16 (m, 4H), 4.08–3.22 (m, 19H), 3.17–3.11 (m, 2H), 3.04–2.99 (m, 2H), 2.82–2.75 (m, 1H), 2.54 (t, J=7.2 Hz, 2H), 2.43–2.39 (m, 1H), 2.16–2.07 (m, 1H), 1.97–1.83 (m, 2H), 1.50–1.45 (m, 2H), 1.32–1.11 (m, 8H).

$^{13}$C NMR (D$_2$O, 75 MHz) δ 173.1, 163.3 (q, J=35.1 Hz), 150.0, 147.3, 127.4, 124.0, 116.9 (q, J=290.7 Hz), 110.9, 96.0, 95.3, 85.9, 80.6, 79.0, 75.4, 74.1, 72.9, 71.6, 71.0, 70.6, 69.9, 68.4, 68.0, 67.7, 61.8, 56.8, 54.1, 51.3, 50.2, 49.3, 48.9, 40.9, 35.3, 34.7, 32.1, 32.0, 30.4, 29.2, 28.4, 27.9.

Example 3

Preparation of Neomycin-Chloramphenicol Heterodimer (n=9) III (Step 1): Preparation of Protected Neomycin-Chloramphenicol Heterodimer 255 mg of the compound of formula 3 (n=9) and 78 mg of Cs$_2$CO$_3$ were added to 2.0 ml of DMF and mixed. 135 mg of the compound of formula 2 dissolved in 1 ml of DMF was added to the obtained solution and then stirred at room temperature for 8 hours. The obtained mixture was poured into water and extracted using 70 ml of EtOAc for 3 times. Then, the extracted organic layer was collected and the organic layer was washed with saturated brine. The washed organic layer was dried with anhydrous Na$_2$SO$_4$ and concentrated in vacuo. The residue was purified with silicagel column chromatography (CH$_2$Cl$_2$:MeOH=15:1) to obtain a white solid protected neomycin-chloramphenicol heterodimer (formula 8 (n=9), 383 mg). The yield is 74%.

$^1$H NMR (CDCl$_3$, 300 MHz) δ 8.12 (d, J=8.5 Hz, 2H), 7.47 (d, J=8.4 Hz, 2H), 7.44 (d, J=7.8 Hz, 1H), 6.18 (br s, 2H), 5.82 (br s, 1H), 5.50–4.95 (m, 8H), 4.15–2.88 (m, 25H), 2.68–2.29 (m, 7H), 1.65–1.23 (m, 70H), 0.97 (s, 9H), 0.94 (s, 9H), 0.13 (s, 3H), 0.12 (s, 3H), 0.09 (s, 3H), −0.13 (s, 3H).

(Step 2): Preparation of Heterodimeric Conjugates of Neomycin-Chloramphenicol 0.25 ml of tetrabutylamoniumfluoride (1.0 M of tetrahydrofuran solution) was added to solution of 157 mg of the compound of formula 8 (n=9) and 1.7 ml of tetrahydrofuran, and then was stirred at room temperature for 2 hours. The obtained mixture was dried and concentrated in vacuo. The residue was dissolved in EtOAc and washed with 0.5 N of hydric acid and saturated brine. The washed residue was dried with anhydrous Na$_2$SO$_4$ and concentrated in vacuo. The concentrated residue was purified with silicagel column chromatography (CH$_2$Cl$_2$:MeOH=15:1) to obtain a white solid compound (99 mg). 3 ml of trifluoroacetic acid was added to the obtained compound and then stirred at room temperature for 1 hour. The mixture was concentrated in vacuo. The residue was filtered using a silicagel column and then purified with semiprep-HPLC (RP-C18 column, H$_2$O comprising 0.1% of TFA:MeCN comprising 0.1% of TFA=70:30) to obtain a salt of trifluoroacetic acid of neomycine-chloramphenicol heterodimer (n=9, 32 mg, solid of white). The yield is 37%.

¹H NMR (D₂O, 300 MHz) δ 8.17 (d, J=8.7 Hz, 2H), 7.58 (d, J=8.7 Hz, 2H), 6.01 (d, J=3.8 Hz, 1H), 5.34 (s, 1H), 5.24 (s, 1H), 5.14 (d, J=2.4 Hz, 1H), 4.36–4.37 (m, 7H), 4.03–3.76 (m, 7H), 3.67–3.00 (m, 12H), 2.82–2.75 (m, 1H), 2.59 (t, J=7.2 Hz, 2H), 2.44–2.24 (m, 1H), 2.18–1.83 (m, 4H), 1.56–1.49 (m, 2H), 1.29–1.09 (m, 14H);

¹³C NMR (D₂O, 75 MHz) δ 173.1, 163.4 (q, J=35.2 Hz), 149.9, 147.3, 127.4, 124.0, 116.8 (q, J=289.9 Hz), 111.0, 96.0, 95.5, 85.9, 80.6, 79.0, 75.5, 74.1, 72.9, 71.5, 71.0, 70.5, 70.0, 68.4, 68.0, 67.8, 61.7, 56.8, 54.1, 51.3, 50.1, 48.8, 41.0, 40.9, 35.3, 32.2, 32.1, 29.3, 28.8, 28.6, 28.5, 28.4, 28.3, 28.2.

Preparation Example 3

Experimental Preparation of Specific RNAs

The RNA of the present invention was prepared with sense DNA of 16S rRNA (sequence listing 1) and an antisense DNA of 16S rRNA (sequence listing 2); a sense DNA of RRE RNA (sequence listing 3) and an antisense DNA of RRE RNA (sequence listing 4); and a sense DNA of TS RNA (sequence listing 5) and an antisense DNA of TS RNA (sequence listing 6).

Paricularily, the two DNAs comprising sense and antisense (2.5 nanomole, respectively), 5×buffer solution (200 mM Tris-HCl, 30 mM MgCl₂, 10 mM spermidine, 50 mM NaCl, pH 7.9; 20 μl), 100 mM DL-dithiotheitol (DTT; 20 μl), four nucleotide tri phosphate mixture (2.5 mM, 20 μl), T7 RNA polymerase (50 units/mL; 1 μl) and diluted water (34 μl) were mixed and cultured at 37° C. for 2 hours. And then 1 unit/ml of Rnase-free RQ1 Dnase was added to the mixture and cultured at 37° C. for 10 minutes. 100 μl of a PCI mixture solution (phenol:chloroform:isopropanol=25:24:1) was added to the obtained mixture, mixed at room temperature for 5 minutes and then centrifuged at 1400 rpm for 10 minutes. The obtained upper solution was poured into a new tube and the RNA was concentrated using the ethanol precipitation method. The obtained RNA was purified by being performed electrphoresis at 6% of polyacrylamide containing 7.0 M urea at a current of 20 mA for 30 minutes. After cutting the RNA band lightened with a UV flashlight and transferring it to a new tube, 500 μl of elution buffer (0.5 M ammonium acetate, 1 mM EDTA, 0.2% SDS, pH 8.0) was added to the mixture and it was left alone at 37° C. for 4 hours. The liquated RNA was transferred to a new tube and purified by phenol extraction and ethanol precipitation. The amount of RNA purified can be certified using a 260 nm UV spectrum.

Experimental Example 1

Determination of Bond Constant Between the Compound of the Present Invention and Specific RNAs The paromomycin bonded with tetramethylrhodamine (hereinafter referred to as "CPR") is used as a luminescence fluorescent probe. The luminescence anisotropy is measured by establishing a thermostat of 20° C. at the Perkin-Elmer LS-50B luminescence spectroscope. The luminescence absorptance of CRP is 510 nm and its luminescence fluorescent is observed at 550 nm. At least 7 measurements were made to obtain one data, wherein the maximum value and the minimum value was excluded and the average of the other 5 measurements was used as a data. The luminescence was measured at an elution buffer using 140 mM NaCl, 5 mM KCl, 1 mM MgCl₂, and 20 mM HEPES pH 7.5. The equation measuring the bond constant (Kd) between CRP and the prepared RNA is represented by the following equation 1:

$$A = A_0 + DNA\{([RNA]_0 + [CRP]_0 + K_d) - ([RNA]_0 + [CRP]_0 + K_d)^2 - 4[RNA]_0[CRP]_0^{1/2}\}/2 \quad \text{(Equation 1)}$$

wherein,

A is the luminescence anisotropy value of CRP when RNA is present, $A_0$ is the luminescence anisotropy value of CRP when RNA is not present, DA is the difference of luminescence anisotropy value when RNA is not present between various RNA concentrations, $[RNA]_0$ is the initial concentration of RNA, $[CRP]_0$ is the initial concentration of CRP, $K_d$ is the bond constant.

If the newly prepared compound is added to the solution after inducing the bonding of the said RNA and CRP, CRP is separated from RNA by a competitive bonding reaction and the compound to be measured achieves a KD value by bonding with RNA. The equation to achieve the KD value is represented by the following equation 2, and $K_d$ and KD are achieved using the non-linear curve fitting method not a linear fitting method. The results are shown in the following table 1.

$$[Aminoglycoside]_0 = \{KD(A_\infty - A_0)/[K_d(A - A_0) + 1]\} \times \{[RNA]_0 - K_d(A - A_0)/(A_\infty - A_0) - [CRP]_0(A - A_0)/(A_\infty - A_0)\} \quad \text{(Equation 2)}$$

wherein,

KD is the bond constant between RNA and the new aminoglycoside, $[Aminoglycoside]_0$ is the initial concentration of aminoglycoside to be measured, A is the luminescence anisotropy value when the bond is being measured, $A_\infty$ is the luminescence anisotropy value when the bonding is completed, $A_0$ is the luminescence anisotropy value when everything is free.

TABLE 1

Comparison of the binding force of heterodimers against each RNA

|  | Neomycin | Preparation 1 | Preparation 2 | Preparation 3 |
|---|---|---|---|---|
| 16s rRNA | >2 | 0.20 | 0.01 | 0.40 |
| RRE RNA | >2 | 0.4 | 0.2 | 0.5 |
| TS RNA | >2 | 2.0 | 2.0 | 2.0 |

As shown in the above table 1, heterodimer compounds (example 1–3) show an improved binding force compared with the neomycin of 16S rRNA or RRE RNA, and an increase in the binding force of general heterodimers is also observed in the present invention. Further, no change was observed in the binding force of TS RNAS, and even the RNAs which showed a change in the binding force displayed various degrees of enhancement in binding force depending on which kind of RNA they are. That is, as for 16S rRNAs, the compound of example 2 showed an increase of more than 200 times of that of neomycin, and RRE RNA showed an increase of about 10 times in binding force. Such results indicate that 16S rRNA, RRE RNA and TS RNA motifs have both stems and loops, and among them 16S rRNA having a specific base sequence showed the highest increase in binding force against heterodimers.

Further, a big difference has been observed depending on the change of the length of the spacer between each heterodimer. Usually, the compound of example 2 wherein the length of the spacer comprises 6 carbons showed the highest increase in binding force. However, this tendency being displayed to the utmost with 16S rRNAs, the compound of example 2 binds with a target molecule, RNA with a specificity at least 20 times of that of the compounds of example 1 or example 3.

As a result, it is proven that the specificity of heterodimers is related to the structure and base sequence comprising the form of the RNA rather than the form of the RNA motif.

Experimental Example 2

Acute Toxicity Experiment on Parenteral Administration of Rats

In order to find out whether the compound of formula 1 has acute toxicity, the following experiment was performed.

A six week old specific pathogen-free (SPF) SD rat was used in the acute toxicity experiment. The neomycin-chloramphenicol heterodimer of the present invention was suspended in 1 ml of physiological saline and administered into the muscles of two rats in the amount of 1 mg/kg. Then, the present inventors observed the life and death of the animal, clinical symptoms, weight variance, and performed haematological examination and blood-biochemical examination. Further, they observed with a naked eye whether there were any changes at the abdominal organ and thoracic organ after performing necropsy of it.

As a result, none of the animals administered with the experimental material showed any specific clinical symptoms or death. Further, toxicity change was not observed in weight variance, haematological examination, blood-biochemical examination, necropsy observations and diagnosis, either. From the above results, it can be concluded that the compound does not show toxicity change till 10 mg/kg, and the oral administration minimum lethal dose ($LD_{50}$) is over 10 mg/kg, and accordingly a safe compound.

INDUSTRIAL APPLICABILITY

As disclosed above, the neomycin-chloramphenicol heterodimers of the present invention shows a stronger binding force with 16S rRNA, RRE RNA and TS RNA compared with neomycin, or chloramphenicol, recognizes both stems and loops of the RNA motif, and also has a specific bond of base sequences comprising RNA. Therefore, the increase of specificity in recognizing RNAs not only enhances the pharmaceutical efficacy of the drug but also enables the neomycin-chloramphenicol heterodimers to be effectively used as an antiviral agent, an antibacterial agent or an anticancer agent due to the reduced side effect which can be caused by non-specific drugs.

SEQUENCE LISTING

<160> NUMBER OF SEQ ID NOS: 6

<210> SEQ ID NO 1
<211> LENGTH: 49
<212> TYPE: DNA
<213> ORGANISM: Artificial Sequence
<220> FEATURE:
<223> OTHER INFORMATION: 16S sense

<400> SEQUENCE: 1
aatttaatac gactcactat agggcgtcac accttcgggt gaagtggcc        49

<210> SEQ ID NO 2
<211> LENGTH: 49
<212> TYPE: DNA
<213> ORGANISM: Artificial Sequence
<220> FEATURE:
<223> OTHER INFORMATION: 16S antisense

<400> SEQUENCE: 2
ggccacttca cccgaaggtg tgacgcccta tagtgagtcg tattaaatt        49

<210> SEQ ID NO 3
<211> LENGTH: 52

-continued

```
<212> TYPE: DNA
<213> ORGANISM: Artificial Sequence
<220> FEATURE:
<223> OTHER INFORMATION: RRE RNA sense

<400> SEQUENCE: 3
aatttaatac gactcactat agggtgggcg cagcttcggc tgacggtaca cc          52

<210> SEQ ID NO 4
<211> LENGTH: 52
<212> TYPE: DNA
<213> ORGANISM: Artificial Sequence
<220> FEATURE:
<223> OTHER INFORMATION: RRE RNA antisense

<400> SEQUENCE: 4
ggtgtaccgt cagccgaagc tgcgcccacc ctatagtgag tcgtattaaa tt          52

<210> SEQ ID NO 5
<211> LENGTH: 58
<212> TYPE: DNA
<213> ORGANISM: Artificial Sequence
<220> FEATURE:
<223> OTHER INFORMATION: TS RNA sense

<400> SEQUENCE: 5
aatttaatac gactcactat aggggccccc ccgccgcgcc atgcctgtgg ccggtcgg    58

<210> SEQ ID NO 6
<211> LENGTH: 58
<212> TYPE: DNA
<213> ORGANISM: Artificial Sequence
<220> FEATURE:
<223> OTHER INFORMATION: TS RNA antisense

<400> SEQUENCE: 6
ccgaccggcc acaggcatgg cgcggcgggg gggcccctat agtgagtcgt attaaatt    58
```

What is clamed is:

1. A neomycin-chloramphenicol heterodimer represented by formula 1:

(formula 1)

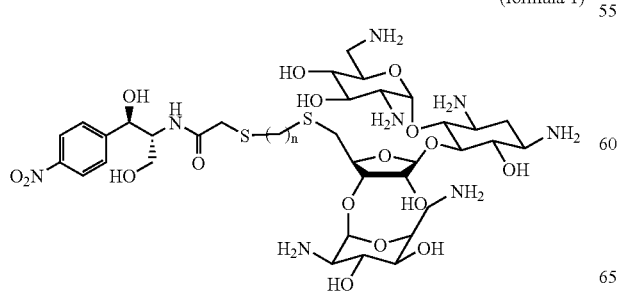

wherein, n is an integer of 2–10.

2. The neomycin-chloramphenicol heterodimer according to claim 1, wherein n is 3, 6 or 9.

3. A method for preparing neomycin-chloramphenicol of claim 1, comprising steps of:

reacting (1R,2R)-2-(9-bromoacetylamido)-1-(4-nitrophenyl)-1,3-t-butyldimethyl-silyloxypropane (formula 2) with the compound of formula 3 in the presence of base to obtain the compound of formula 8 (step 1), and reacting the obtained compound of formula 8 with a deprotecting agent to prepare the neomycin-chloraniphenicol heterodimer of claim 1 (step 2):

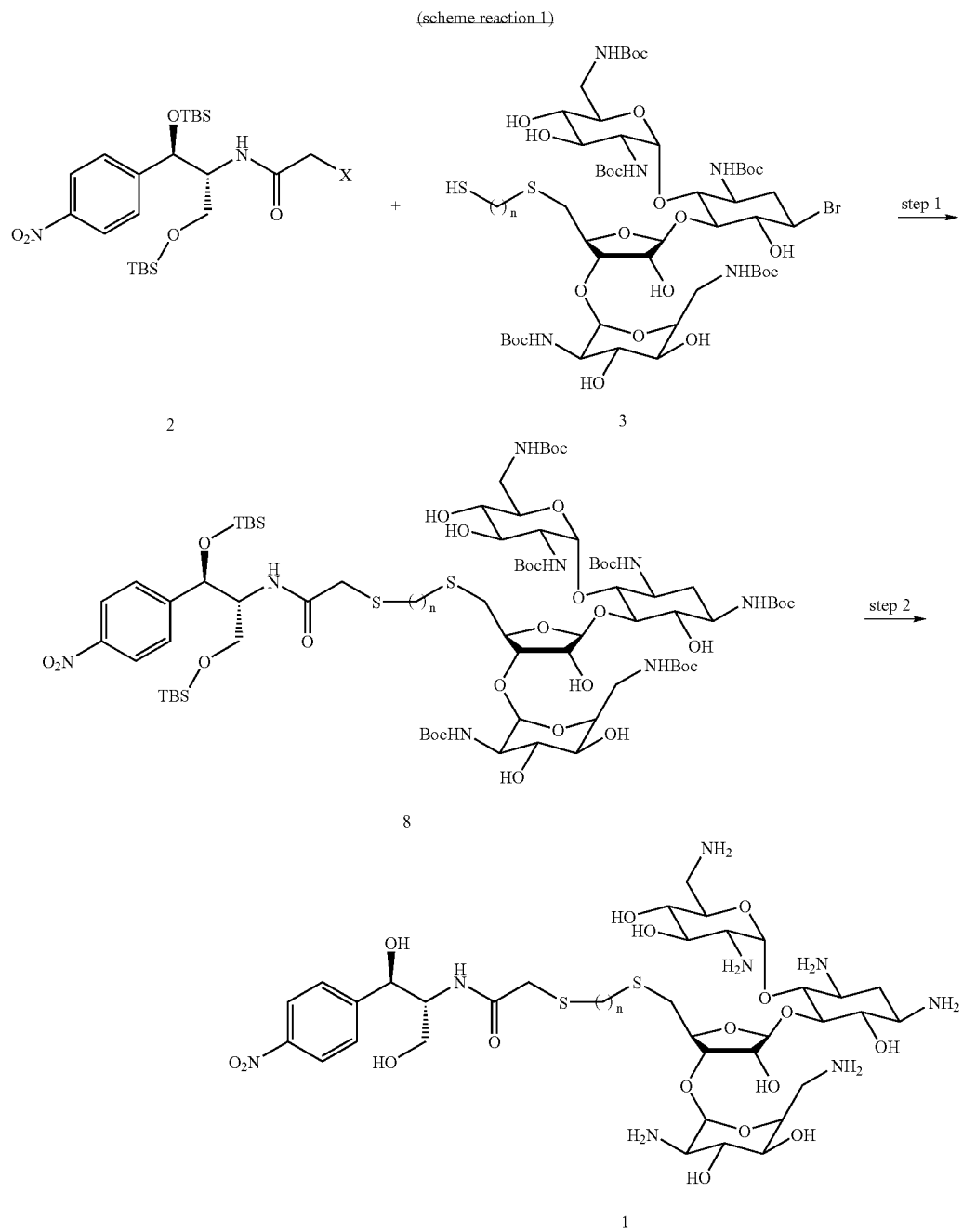

wherein, n is an integer of 2–10.

4. The method according to claim 3, wherein the base of step 1 is $K_2CO_3$, $Na_2CO_3$ or $Cs_2CO_3$.

5. The method according to claim 3, wherein the deprotecting agent of step 2 is tetrabutylammoniumfluoride, hydrofluoric acid, hydrofluoric acid pyridine salt, hydrochloric acid, sulfuric acid, acetic acid or trifluoroacetic acid.

6. An antiviral agent, an antibacterial agent or an anticancer drug containing neomycin-chlorampherinicol heterodimer of claim 1 as an active ingredient.

* * * * *